(12) United States Patent
Sasaki et al.

(10) Patent No.: US 6,770,065 B1
(45) Date of Patent: Aug. 3, 2004

(54) FASTENER AND ABSORBING ARTICLE USING IT

(75) Inventors: Jun Sasaki, Tochigi (JP); Manabu Matsui, Tochigi (JP); Manabu Kaneta, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/701,009

(22) PCT Filed: Apr. 15, 1999

(86) PCT No.: PCT/JP99/02009

§ 371 (c)(1),
(2), (4) Date: Nov. 22, 2000

(87) PCT Pub. No.: WO99/60881

PCT Pub. Date: Dec. 2, 1999

(30) Foreign Application Priority Data

| May 26, 1998 | (JP) | ............................................. 10-144222 |
| May 26, 1998 | (JP) | ............................................. 10-144223 |
| Jun. 16, 1998 | (JP) | ............................................. 10-168764 |

(51) Int. Cl.[7] .......................... A61F 13/15; A44B 18/00
(52) U.S. Cl. ..................... 604/391; 604/385.01; 24/442
(58) Field of Search .......................... 24/452, 451, 450, 24/449, 448, 447, 446, 445, 444, 442, 443, 305, 572.1, FOR 100; 604/385.01, 391

(56) References Cited

U.S. PATENT DOCUMENTS

| 4,846,815 A | * | 7/1989 | Scripps ....................... 604/391 |
| 5,326,612 A | * | 7/1994 | Goulait ....................... 428/100 |
| 5,383,872 A |   | 1/1995 | Roessler et al. |
| 5,515,583 A |   | 5/1996 | Higashinaka |
| 5,614,281 A |   | 3/1997 | Jackson et al. |
| 5,647,864 A | * | 7/1997 | Allen et al. .................. 604/391 |
| 5,692,271 A |   | 12/1997 | Provost et al. |
| 5,761,775 A | * | 6/1998 | Legome et al. ............... 24/450 |
| 5,868,987 A | * | 2/1999 | Kamfer et al. .............. 264/280 |
| 5,913,482 A | * | 6/1999 | Akeno ......................... 24/452 |

FOREIGN PATENT DOCUMENTS

| JP | 6507799 | 11/1992 |
| JP | 633359 | 2/1994 |
| JP | A6133808 | 5/1994 |
| JP | A6507800 | 9/1994 |
| JP | 6-507800 | 9/1994 |
| JP | 7171011 | 7/1995 |
| JP | 7313213 | 12/1995 |
| JP | 09-195154 | 7/1997 |
| JP | A9195154 | 7/1997 |
| JP | 10-121359 | 5/1998 |
| JP | A10121359 | 5/1998 |

\* cited by examiner

*Primary Examiner*—Gary L. Welch
*Assistant Examiner*—Jeanette Chapman
(74) *Attorney, Agent, or Firm*—Birch, Stewart, Kolasch & Birch, LLP

(57) ABSTRACT

The fastener of the present invention comprises a male material, having many hooks, of a mechanical fastener and a female material, made of nonwoven fabric, of the mechanical fastener, the male material engaging said female material, wherein many hooks (3) in the male material (1) have a density of 100 to 1000 pieces/cm$^2$, a height of 300 to 1500 μm and a width of 100 to 500 μm, and the nonwoven fabric composing the female material has a basis weight of 20 to 80 g/m$^2$ and a fineness, of 4 to 15 deniers, of a composite fiber thereof. The fastener of is used, for example, in a disposable diaper of absorbent articles.

9 Claims, 8 Drawing Sheets

FASTENER AND ABSORBING ARTICLE USING IT

This application is the national phase under 35 U.S.C. §371 of PCT International Application No. PCT/JP99/02009 which has an International filing date of Apr. 15, 1999, which designated the United States of America.

TECHNICAL FIELD

This invention relates to a fastener which has a high engaging force, which generates fluffing only very slightly and which is prevented from being lowered in engaging force after repeated attachment and detachment. It also relates to an absorbent article using such a fastener.

BACKGROUND ART

Heretofore, fasteners of the type comprising a male material and a female material of a mechanical fastener have been used in various fields including the field of absorbent articles such as disposable diapers because of the reasons that repeated attachment and detachment is possible and they have a proper engaging force. In general, as a female material of such a mechanical fastener, those fabrics, which can be obtained by knitting many fibers into a loop pattern or an arch pattern on a base seat, are used. However, since such fabrics exhibit a comparatively stiff feel, the base material is deteriorated in feel when they are adhered to the base material. Moreover, since the manufacturing process is complicated, productivity becomes low and cost becomes high.

In order to obviate such problems, there have been made several proposals of a nonwoven fabric composed by forming a loop on its single surface side by way of needle punch, span bond, span race or heat contraction (Japanese Patent Laid-Open Publication Nos. 06-33359, 07-171011, 07-313213, etc.). However, those proposed nonwoven fabrics are, when compared with knitted fabrics, generally low in degree of freedom (movability of fibers) and hardly wrapped with male materials. Accordingly, it is difficult to obtain sufficient engaging force. There has also been proposed a female material using spun bond or the like, in which strength in joining point between fibers is reduced in order to enhance the degree of freedom. Although such a female material has sufficient engaging force, it has such shortcomings that fluffing is heavily generated, lowering of engaging force occurrable when repeated detachment is made is significant, and the problems of productivity and cost are not yet completely solved.

It is, therefore, an object of the present invention to provide a fastener comprising a mechanical fastener which has a high engaging force and which generates fluffing only very slightly, and an absorbent article using the same.

It is another object of the present invention to provide a fastener comprising a mechanical fastener in which an engaging force is not lowered when repeated attachment and detachment is made, and an absorbent article using the same.

It is a further object of the present invention to provide a fastener comprising a mechanical fastener which is high in productivity and which can be manufactured at a low cost, and an absorbent article using the same.

DISCLOSURE OF THE INVENTION

The inventors of the present invention have found out that the generation of fluffing can be prevented by using a specific nonwoven fabric as a female material of a mechanical fastener and that an engaging force can be enhanced by using the female material in combination with a male material which is provided, at a specific density, with hooks having a specific configuration, thus enabling to achieve the above objects.

The present invention have been accomplished based on the above finding. According to the present invention, there is provided, in order to achieve the above objects, a fastener comprising a male material, having many hooks, of a mechanical fastener and a female material, made of nonwoven fabric, of the mechanical fastener, the male material engaging the female material, wherein many hooks in the male material have a density of 100 to 1000 pieces/cm$^2$, a height of 300 to 1500 $\mu$m and a width of 100 to 500 $\mu$m.

According to another version of the present invention, there is provided, in order to achieve the above objects, an absorbent article comprising a liquid-permeable topsheet, a liquid-impermeable backsheet and a liquid-retentive absorbent core interposed between the topsheet and the backsheet, a fastening tape for the use of securement being arranged at each of opposing left and right side edge regions of a back-side zone, a landing tape capable of being secured to the fastening tape being arranged at a stomach-side zone, wherein a male material, having many hooks, of a mechanical fastener is used as the fastening tape, the many hooks having a density of 100 to 1000 pieces/cm$^2$, a height of 300 to 1500 $\mu$m and a width of 100 to 500 $\mu$m, and a female material, made of nonwoven fabric, of the mechanical fastener is used as the landing tape or otherwise, the female material is used as the fastening tape and the male material is used as the landing tape.

BRIEF DESCRIPTION OF THE DRAWINGS

FIG. 1(a) is an enlarged perspective view of an essential portion of the male material and FIG. 1(b) is a vertical sectional view of a hook of the male material;

BEST MODE FOR CARRYING OUT THE INVENTION

A fastener according to the present invention comprises a male material, having many hooks, of a mechanical fastener and a female material, made of nonwoven fabric, of the mechanical fastener. The male and female materials are fastened by causing the hooks in the male material to engage a fiber in the female material. Such male and female materials will be described hereinafter.

Figure 1:
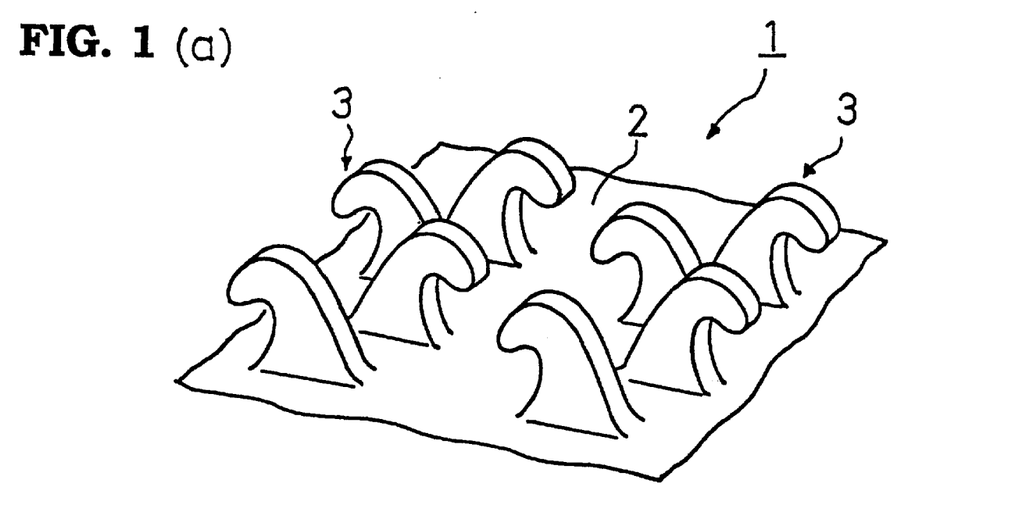
FIG. 1 is an illustration showing one example of a male material in a fastener of the present invention.

First, the male material is described with reference to FIG. 1. FIG. 1 is an illustration showing one example of a male material in a fastener of the present invention, FIG. 1(a) shows an enlarged perspective view of an essential portion of the male material and FIG. 1(b) shows a vertical sectional view of a hook in the male material.

As shown in FIGS. 1(a) and 1(b), a male material 1 comprises a base material 2 and many hooks 3 raised from one surface of the base material 2. Each hook 3 comprises a stem portion 4 continuous with the base material 2 and a swollen portion 5 swelling sideways from an upper portion of the stem portion 4. The hooks 3 are regularly arranged on the base material 2 in multiple rows. The hooks 3 on each row are arranged such that the swollen portions 5 are oriented in the same direction. Moreover, the hooks 3 are arranged such that the swollen portions 5 on a certain row are mutually alternately oriented with respect to the swollen portions 5 on the adjacent row.

Existing density of the hooks 3 on the base material 2 is 100 to 1000 pieces/cm$^2$, preferably, 100 to 600 pieces/cm$^2$ and particularly preferably 200 to 500 pieces/cm$^2$ at any region of the male material 1. If the existing density of the hooks 3 is less than 100 pieces/cm$^2$, the total number of fibers laid over the swollen portions 5 is reduced and a sufficient engaging force is unobtainable. In contrast, if the existing density of the hooks 3 is more than 1000 pieces/cm$^2$, it becomes difficult for the hooks 3 to enter the female material and a sufficient engaging force is unobtainable.

As shown in FIG. 1(b), the hooks 3 are each 300 to 1500 cm, preferably 320 to 1000 $\mu$m and particularly preferably 350 to 600 $\mu$m in height H. If the height H is less than 300 $\mu$m, the hooks cannot enter the nonwoven fabric deep enough and a sufficient engaging force is unobtainable. In contrast, if the height H is more than 1500 $\mu$m, it becomes necessary to increase rigidity of each hook in order to obtain a sufficient engaging force. This follows that irritation to the user's skin is increased. The height H of each hook 3, as shown in FIG. 1(b), refers to a distance between an upper surface of the base material 2 and a lower surface of the swollen portion 5.

As shown in FIG. 1(b), the hooks 3 are each 100 to 500 $\mu$m, preferably 120 to 400 $\mu$m and particularly preferably 130 to 300 $\mu$m in width D. If the width D is less than 100 $\mu$m, the total number of the fibers laid over the swollen portion 5 is reduced and a sufficient engaging force is unobtainable. In contrast, if the width D is more than 500 $\mu$m, it becomes difficult for the hook 3 to enter between the adjacent and a sufficient engaging force is unobtainable. The width D of each hook 3, as shown in FIG. 1(b), refers to a width of the swollen portion 5 swelling sideways from the stem portion 4.

By using the male material having such hooks of a specific configuration at a specific density in combination with a female material as later described, the fastener according to the present invention can have a high engaging force and generates fluffing only very slightly. Moreover, decrease in engaging force, which would otherwise occur after repeated attachment and detachment, can be prevented effectively.

Figure 2:
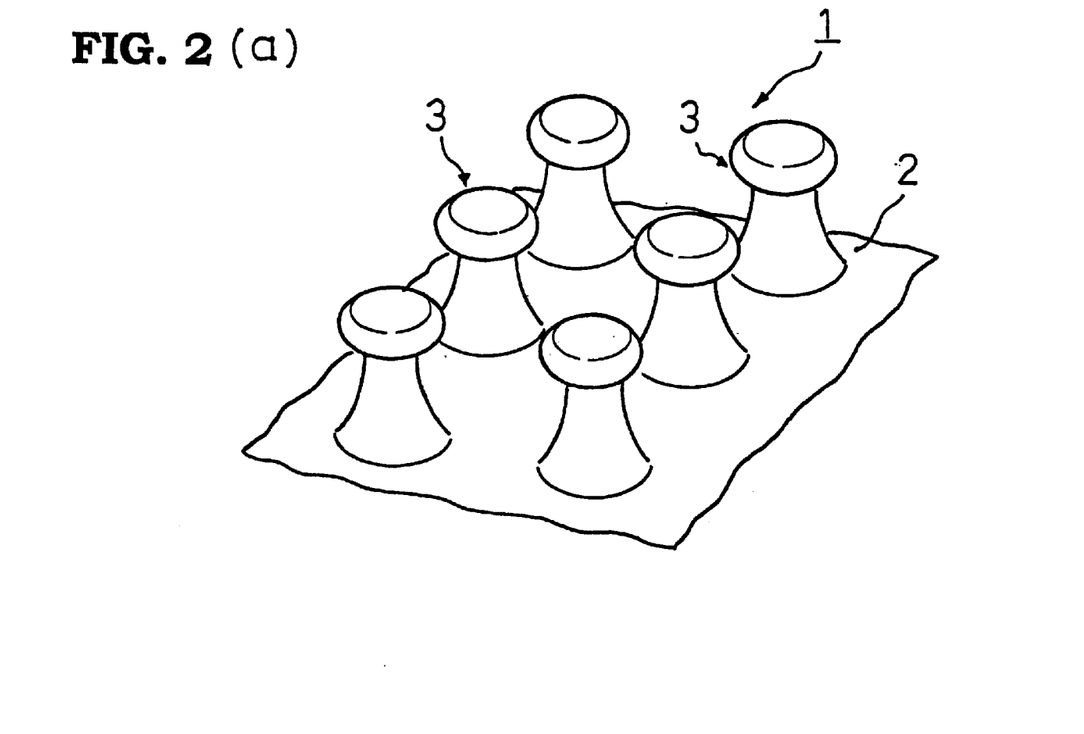
FIG. 2 is an illustration (corresponding to FIG. 1) showing another example of the male material.
Figure 3:
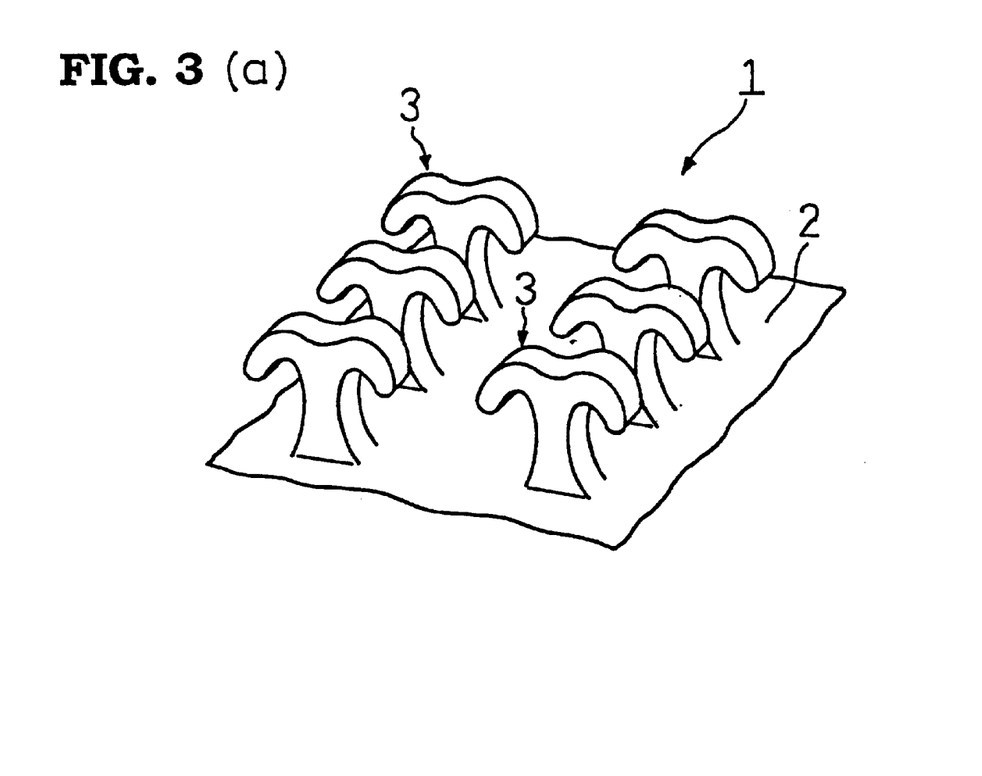
FIG. 3 is an illustration (corresponding to FIG. 1) showing a further example of the male material

As a male material used in the fastener according to the present invention, those shown in FIGS. 2 and 3, as well as in FIG. 1, can be used. The male materials 1 shown in FIGS. 2(a) and 2(b) have many mushroom-like hooks 3. The male materials 1 shown in FIGS. 3(a) and 3(b) have many T or Y-shaped hooks 3. For any of those male materials, the existing density of the hooks 3, the height H of the hooks and the width D of the hooks are in the above-mentioned ranges. It should be noted, however, the calculation of the existing density of the hooks in the male material shown in FIGS. 2 and 3 is different from that shown in FIG. 1. Since the hooks in the male material of FIGS. 2 and 3 have the swollen portions 5 which are swollen at least in two directions, one hook is regarded as two in calculation of the existing density. That is to say, one hook 3 in the male material 1 shown in FIGS. 2 and 3 has an engaging force equal to or greater than the engaging force of two hooks in the male material shown in FIG. 1. For this reason, the fastener using the hooks 3 of FIGS. 2 and 3 are particularly preferably used.

A female material according to the present invention, which is used in combination with the above male material, will now be described. The female material is made of nonwoven fabric.

The nonwoven fabric is preferably a nonwoven fabric A having a basis weight of 20 to 80 g/m$^2$, a fineness, of 4 to 15 deniers, of the fibers composing the nonwoven fabric. In a nonwoven fabric used for a female material of this type, fibers, which are comparatively high in degree of freedom as a composite fiber and which have a thin denier size of about 1 to 2 deniers in fineness, have heretofore been mostly used in order to increase the engaging property with respect to a male material. However, if a female material of a mechanical fastener is composed using a nonwoven fabric which is composed of fibers having such a thin denier size, there is encountered with such an inconvenience that fluffing is heavily generated due to reduced strength in joining point between fibers. In view of the above, the present invention employs, in order to obviate the above inconvenience, a nonwoven fabric A, as a female material, which is composed of fibers having a thicker denier size than those of the conventional one. However, since the fibers having a thick denier size are lower in degree of freedom than the fibers having a thin denier size, use of the nonwoven fabric A composed of fibers having a thick denier size as a female material tends to decrease the engaging performance with respect to the male material. In the present invention, a high engaging force can be obtained by using the nonwoven fabric A composed of fibers having a thick denier size as a male material. As a result, the fastener according to the present invention becomes to have a high engaging force and generates fluffing only very slightly. Moreover, since fluffing is generated only very slightly, decrease in engaging force, which would otherwise occur after repeated attachment and detachment, can be prevented effectively. Furthermore, since the above female material can easily be manufactured when compared with the conventionally-used female material which is composed of a knitted fabric, productivity is high and the manufacturing cost is low.

The fineness of fibers composing the nonwoven fabric A will be described in more detail. If the fineness is less than 4 deniers, fluffing is heavily generated when the male material is detached from the female material. And the engaging force is decreased when attachment and detachment is made. In contrast, if it is more than 15 deniers, the degree of freedom of the fibers is lowered, thus resulting in many inconveniences such as, the male material comes to get difficulty in engagement, the engaging force is reduced, productivity is lowered, and processing performance is degraded. The fineness is preferably 5 to 12 deniers and more preferably 6 to 12 deniers.

The fibers composing the nonwoven fabric A is preferably 3 cN or more and more preferably 5 cN or more in strength of the joining point of main fibers thereof. Those requirements (or limitations) are entered in consideration of breakage of the joining point of each composite fiber, fluffing and the like which occur when the male material is detached from the female material in the case where the nonwoven fabric A employed in the present invention is used as a female material of the mechanical fastener. The term "main composite fiber" used herein refers to those, of all the fibers composing the nonwoven fabric A, which are percentage-wise mostly used. Accordingly, in the case where the nonwoven fabric A is composed of a single kind of fibers, the strength of the joining point refers to a strength of joining point of the fibers. In the case where the nonwoven fabric A is composed of two or more kinds of fibers, it refers to strength of a joining point of those fibers which are percentage-wise mostly used, the strength being measured in combination of those fibers.

Figure 4:
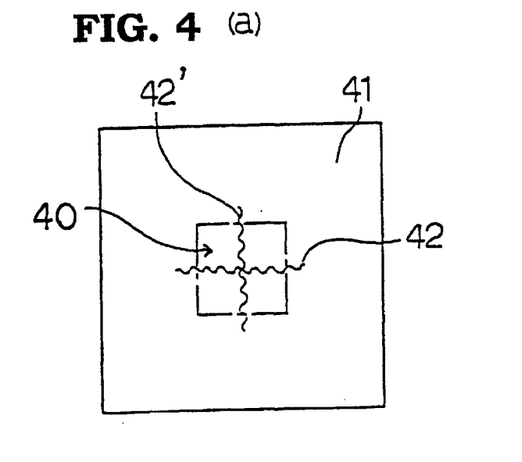
FIG. 4 is an illustration showing a method for measuring strength in joining point.

The method for measuring strength of the joining point will now be described with reference to FIG. 4.

First, two fibers 42, 42' are placed on a form paper 41 having a cut 40 of a regular square configuration formed in its central area as shown in FIG. 4(a), such that the fibers 42, 42' are intersected with each other at right angles and the intersection point is located at the center of the cut 40. Then, the fibers 42, 42' are fixedly secured to the form paper 41 through adhesive agent. Then, the intersection point of the two fibers are joined together under the same conditions as in the manufacture of the nonwoven fabric. This joining means may include, for example, adhesion using adhesive agent and heat fusion using hot blast heat welding. Then, the form paper 41 is cut along dot lines shown in FIG. 4(b) to obtain two regular square cut pieces 43, 43' in which end portions of each fiber are adhered. Then, the respective cut pieces 43, 43' are pulled at a speed of 50 mm/min in a direction as indicated in FIG. 4(c) to measure the strength of the intersection point. A value thus measured serves as a joining point strength (cN).

In the nonwoven fabric A, it is preferably that all of the composite fibers satisfy the above-mentioned requirements (or limitations) of the fineness and the joining point strength. It should be noted, however, that only if at least the main composite fibers, preferably those fibers occupying 50 wt. % or more and particularly preferably those fibers occupying 60 wt. % or more satisfy the above-mentioned requirements (or limitations) of the fineness and the joining point strength, desired results can be obtained.

The nonwoven fabric A has a basis weight of 20 to 80 g/m$^2$, preferably 25 to 70 g/m$^2$ and more preferably 30 to 60 g/m$^2$. If the basis weight is less than 20 g/m$^2$, a sufficient space for the male material to engage the female material cannot be obtained and breakage occurs to the nonwoven fabric when the male material is detached. In contrast, if the basis weight is more than 80 g/m$^2$, although the function as the female material is not adversely affected, productivity of the nonwoven fabric is lowered and the cost is increased. The nonwoven fabric A has a thickness of preferably 0.5 to 2.0 mm and particularly preferably 1.0 to 2.0 mm (under a load of 0.15 g/cm$^2$).

As the nonwoven fabric A, any material can be used inasmuch as the above conditions are satisfied and without any particular limitation in its kind. The examples may include an airthrough nonwoven fabric, a spunbond nonwoven fabric, a heatroll nonwoven fabric, a chemical bond nonwoven fabric and the like. Particularly preferably, an airthrough nonwoven fabric as a nonwoven fabric which is bulky and which has a high degree of freedom, is used.

In order further restrain the generation of fluffing of the nonwoven fabric A, the nonwoven fabric A may be subjected to embossing treatment or the like.

The nonwoven fabric composing the female material of the present invention is preferably a nonwoven fabric B which is composed by laminating an engagement layer engaged with the male material and an adhesive layer adhered to a base material, in which the engagement layer and the adhesive layer are composed of an airthrough nonwoven fabric, and in which a fineness of a main fiber composing the engagement layer is larger than a fineness of a main fiber composing the adhesive layer.

The nonwoven fabric, which has heretofore been used as a female material of this type, has an additional problem in that adhesive agent tends to exude when the adhesive agent is adhered to the base material, aside from the above-mentioned problems in that the engaging force is not sufficient, fluffing is greatly generated, productivity is low and the cost is high.

By using the nonwoven fabric B as the nonwoven fabric composing the female material, there can be provided a fastener in which a bulky engagement surface can be obtained, as a result, an engaging force with respect to a male material is high, fluffing is generated only very slightly, adhesive agent does not exude when the nonwoven fabric is adhered to a base material through adhesive agent and productivity is high, and an absorbent article, using the fastener, which is nice fit.

Figure 5:
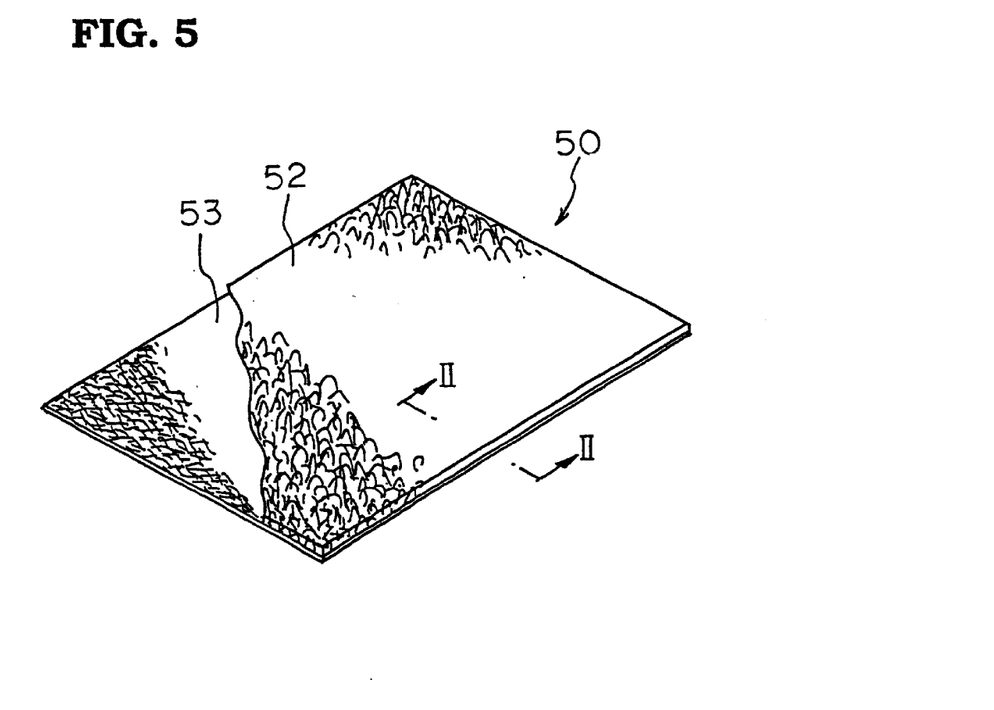
FIG. 5 is a perspective view showing one embodiment of a nonwoven fabric composing the fastener of the present invention.
Figure 6:
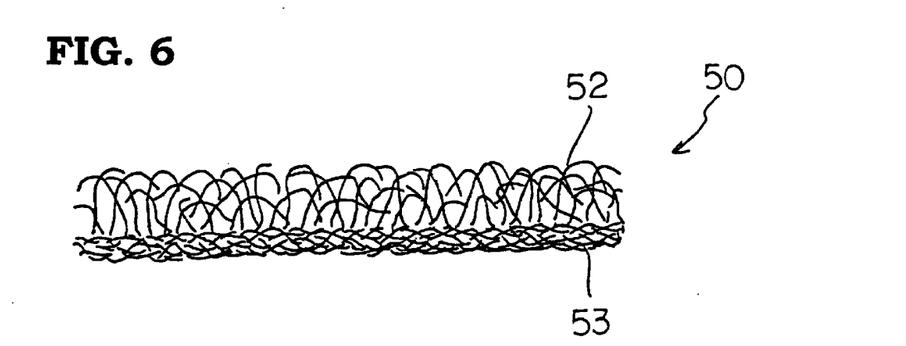
FIG. 6 sectional view taken on line II—II of FIG. 5.

The nonwoven fabric B (50) shown in FIGS. 5 and 6 is a nonwoven fabric for a female material of a mechanical fastener. It is composed by laminating an engagement layer 52 engaged with a male material of the mechanical fastener and an adhesive layer 53 adhered to a base material. The term "base material" herein used refers to an object which is to be adhered to the nonwoven fabric B of the present invention. The examples may include a backsheet, etc., of a disposable diaper as later described.

Both the engagement layer 52 and the adhesive layer 53 are made of an airthrough nonwoven fabric. The fineness of the main fibers composing the engagement layer 52 is larger than the fineness of the main fibers composing the adhesive layer 53.

If the fineness of the main fibers composing the engagement layer 52 is equal to or less than the fineness of the main fibers composing the adhesive layer 53, it becomes difficult to obtain a sufficient force, as a female material of a mechanical fastener, the force enough to be detached from a male material.

This will be described in more detail. The engagement layer 52 has a basis weight of preferably 10 to 60 g/m$^2$ and more preferably 20 to 40 g/m². The adhesive layer 53 has a basis weight of preferably 5 to 60 g/m² and more preferably 10 to 30 g/m². The nonwoven fabric B, as a whole, has an air permeability of preferably 380 cc/(cm²·sec) or less and more preferably 350 cc/(cm²·sec) or less.

If the basis weight of the engagement layer 52 is less than 10 g/m², a sufficient space for the male material to wrap over the female material is difficult to maintain. Moreover, breakage occurs to the nonwoven fabric when the male material is detached. In contrast, if the basis weight is more than 60 g/m², although the function as the female material is not adversely affected, productivity of the nonwoven fabric is lowered and the cost is increased.

If the basis weight of the adhesive layer 53 is less than 5 g/m², the adhesive agent tends to exude when the nonwoven fabric is adhered to the base material through adhesive agent. In contrast, if the basis weight is more than 60 g/m², it is not preferable in respect of productivity of the nonwoven fabric and cost as in the case with the engagement layer.

If the air permeability is more than 380 cc/cm², the adhesive agent tends to exude when the nonwoven fabric is adhered to the base material through adhesive agent. Moreover, the plane (or surface) for adhesion with respect to the base material is reduced. Accordingly, the force for adhesion with respect to the base material is reduced.

Two nonwoven fabrics B are overlapped one upon the other and air permeability thereof is measured by Method A of JIS-L-1096.

The engagement layer 52, as mentioned above, is a layer composed of an airthrough nonwoven fabric. The main fibers are fibers which exist 50 wt. % or more with respect to the total composite fibers of the engagement layer 52. The engagement layer 52 may be composed of only the main fibers.

That is to say, the engagement layer 52 is a layer composed of an airthrough nonwoven fabric which is obtained by subjecting a fiber web composed of the main fibers or a mixture of the main fibers of 50 wt. % or more and other fibers to the known airthrough treatment.

The fineness of the main fibers of the engagement layer 52 is not particularly limited inasmuch as it is larger than the fineness of the main fibers of the adhesive layer 53. However, the fineness of the main fibers of the engagement layer 52 is preferably 2 to 15 d and more preferably 5 to 10 d. The fiber length is preferably 30 to 100 mm and more preferably 40 to 80 mm.

The main fibers of the engagement layer 52 has a joining point strength, caused by fusing the main fibers themselves, of preferably 3 cN or more and more preferably 5 cN or more. If the joining point strength is 3 cN or less, breakage of the fusing point of each composite fiber occurs when the nonwoven fabric B of the present invention is used as a female material of the mechanical fastener. This results in a cause for generation of fluffing.

The above-mentioned joining point strength is measured generally in the same method as the method for measuring the joining point strength of the fibers themselves which compose the nonwoven fabric A.

Two fibers are placed on a form paper having a cut of a regular square configuration formed in its central area such that the fibers are intersected with each other at right angles and the intersection point is located at the center of the cut. Then, the fibers are fixedly secured to the form paper through adhesive agent. Then, the form paper with the fibers adhered thereto is subjected to heat treatment by supplying a hot air of a processing temperature of 143° C. for 12 seconds at a velocity of 2.3 m/sec.

The form paper, in which the respective fibers are heat treated and adhered by heating, is cut along a square slit to obtain two square cut pieces in which end portions of the respective fibers are adhered thereto. Then, the respective cut pieces are pulled at a speed of 50 mm/min in a direction for intersecting the cut pieces at right angles to measure the strength of the intersection point. A value thus measured serves as a joining point strength.

On the other hand, the adhesive layer 53, as mentioned above, is a layer composed of an airthrough nonwoven fabric. The main fibers are fibers which exist 50 wt. % or more with respect to the total composite fibers of the adhesive layer 53. The adhesive layer 53 may be composed of only the main fibers.

That is to say, the adhesive layer 53 is a layer composed of an airthrough nonwoven fabric which is obtained by subjecting a fiber web composed of the main fibers or a mixture of the main fibers of 50 wt. % or more and other fibers to the known airthrough treatment.

The fineness of the main fibers of the adhesive layer 53 is not particularly limited inasmuch as it is smaller than the fineness of the main fibers of the engagement layer 52. However, the fineness of the main fibers of the adhesive layer 53 is preferably 0.5 to 5 d and more preferably 2 to 3 d. The fiber length is preferably 30 to 100 mm and more preferably 40 to 80 mm.

Since the nonwoven fabric B according to this embodiment is constructed in the manner as described above, it has a high engaging force with respect to the male material and generates fluffing only very slightly. Moreover, adhesive agent does not exude when the nonwoven fabric B is adhered to a base material through adhesive agent and productivity is high.

The nonwoven fabric B according to this embodiment can be manufactured in the following manner. The nonwoven fabric B can easily be obtained through the airthrough process in which after a fiber web is formed in accordance with a normal method, a hot air of 120 to 150° C. is supplied to the fiber web for 5 to 10 seconds at a velocity of 1 to 2 m/sec.

It should be noted that the nonwoven fabric B according to the present invention is not composed of only two layers, for example, of the engagement layer and the adhesive layer but an additional layer (multilayer is also accepted) may be present between the engagement layer and the adhesive layer.

The nonwoven fabric, composing the female material, of the present invention is composed by subjecting a raw nonwoven fabric to embossing treatment and elongation thereof, at the time when a load of 2 N/25 mm is incurred in a CD direction, is preferably 75% or less of the raw nonwoven fabric.

By using the nonwoven fabric C as the nonwoven fabric composing the female material, there can be provided a fastener in which an engaging force with respect to a male material is high when it is used as a female material of a mechanical fastener, fluffing is generated only very slightly by subjecting it to embossing treatment, and productivity is high, and an absorbent article, using the fastener, which is nice fit.

That is, the nonwoven fabric C according to this embodiment is composed by subjecting a raw nonwoven fabric to embossing treatment and characterized in that elongation thereof, at the time when a load of 2 N/25 mm is incurred in a CD direction, is 75% or less of the raw nonwoven fabric. It should be noted that the lowermost limit is not particularly defined. If the elongation is more than 75%, the strength of the entire nonwoven fabric is not sufficient when the male material is detached and in addition, it turns out to be a cause for generating fluffing. Accordingly, the above-mentioned limitation is necessary.

The elongation is measured in the following manner. A striplike sample having a width of 25 mm and a length of 100 mm is prepared, the same is subjected to a tensile test under the conditions of 75 mm in chuck-to-check distance using a Tensilon tensile test machine and the expansion of the sample under a load of 2 N is measured. Presuming that this expansion is a mm, the elongation can be obtained from the following equation.

$$\text{elongation} = (a/75) \times 100 \quad (\%)$$

This will be described in more detail. The nonwoven fabric C according to this embodiment has a thickness of preferably 0.4 mm or more and more preferably 0.5 mm or more. The raw nonwoven fabric is preferably an airthrough nonwoven fabric. The thickness used herein refers to a thickness when a pressure of 12 Pa is applied to the nonwoven fabric C. If the thickness is less than 0.4 mm, a sufficient space for the male material of the mechanical fastener to wrap over the female material cannot be maintained.

The nonwoven fabric C has a basis weight of preferably 10 to 100 g/m$^2$ and more preferably 20 to 60 g/m$^2$. If the basis weight of the nonwoven fabric is less than 10 g/m$^2$, a sufficient space for the male material to wrap over the female material cannot be maintained and breakage occurs to the nonwoven fabric when the male material is detached. In contrast, if the basis weight is more than 100 g/m$^2$, productivity of the nonwoven fabric is lowered and the cost is increased.

The raw nonwoven fabric is preferably an airthrough nonwoven fabric. It is a nonwoven fabric composed of only main fibers or a fiber mixture of the main fibers and other fibers. That is, it is preferred that the nonwoven fabric C according to this embodiment is composed by subjecting an airthrough nonwoven fabric, as a raw nonwoven fabric, to embossing treatment which airthrough nonwoven fabric is obtained by subjecting the fiber web composed of only the main fiber or the fiber mixture to the normally known airthrough treatment. It should be noted that a mixing ratio of the main fiber in the fiber mixture is preferably 50 wt. % or more in the entire fiber mixture.

A fineness of the main fiber is preferably 2 to 15d and more preferably 5 to 10 d. A fiber length of the main fiber is preferably 30 to 100 mm and more preferably 40 to 80 mm.

In the nonwoven fabric C according to this embodiment, it is preferable in view of satisfaction to the above elongation and restraining effect of fluffing that the emboss pattern formed by the embossing treatment is formed at least over the entire width of the nonwoven fabric C only excluding opposite sides thereof and in such a manner as to intersect with the MD direction. Specific examples of the emboss pattern will now be described with reference to FIGS. 7 to 14.

Figure 7:
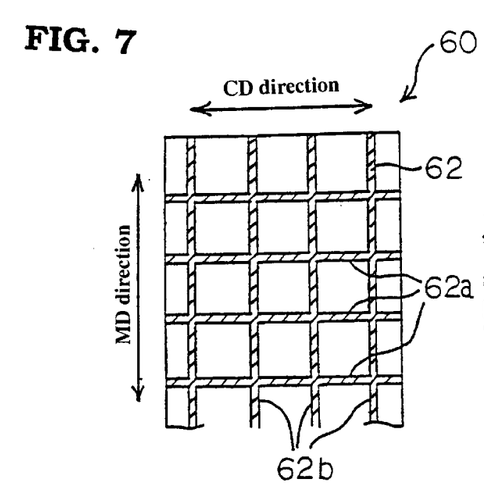
FIG. 7 is a perspective view showing another embodiment of a nonwoven fabric composing the fastener of the present invention.

In the nonwoven fabric C (60) shown in FIG. 7, the emboss pattern is of lattice. That is, in this embodiment, a lattice-like emboss pattern is formed by emboss lines 62a formed in parallel to the CD direction of the nonwoven fabric C (60) and emboss lines 62b formed in parallel to the MD direction. By those emboss lines 62a, a lattice-like emboss pattern is formed over the entire width of the nonwoven fabric C and in such a manner as to intersect with the MD direction.

Figure 8:
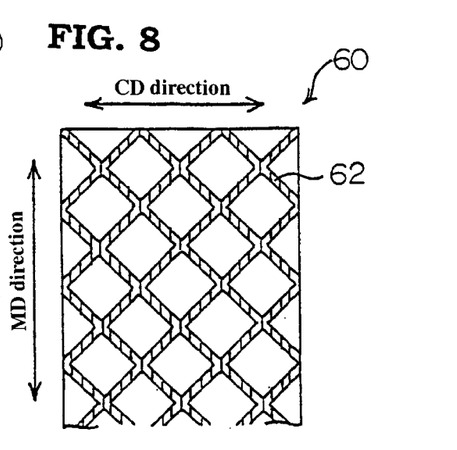
FIG. 8 is a perspective view showing still another embodiment of a nonwoven fabric composing the fastener of the present invention.

In the nonwoven fabric C (60) shown in FIG. 8, the emboss pattern is of lattice and each emboss line 62 is formed in a slantwise direction of the nonwoven fabric C. Because of the feature that each emboss line is formed in the slantwise direction of the nonwoven fabric C, the emboss pattern is formed over the entire width of the nonwoven fabric C and in such a manner as to intersect with the MD direction. As seen, the emboss pattern is not particularly limited in intersection angle with respect to the MD direction inasmuch as each emboss line intersects with the MD direction of the nonwoven fabric C.

Figure 9:
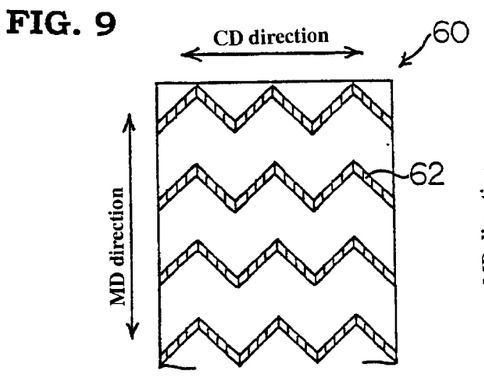
FIG. 9 is a perspective view showing still another embodiment of a nonwoven fabric composing the fastener of the present invention.

In the nonwoven fabric C (60) shown in FIG. 9, the emboss pattern is formed over the entire width of the nonwoven fabric C by forming zigzag-shaped (wavy) emboss lines 62 widthwise (CD direction) over the entire area of the nonwoven fabric C.

Figure 10:
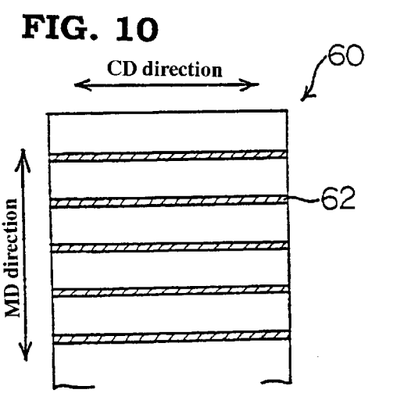
FIG. 10 is a perspective view showing still another embodiment of a nonwoven fabric composing fastener of the present invention.

In the nonwoven fabric C (60) shown in FIG. 10, the emboss pattern is formed over the entire width of the nonwoven fabric C by forming linear emboss lines 62 Gin parallel to the CD direction widthwise (CD direction) over the entire area of the nonwoven fabric C.

Figure 11:
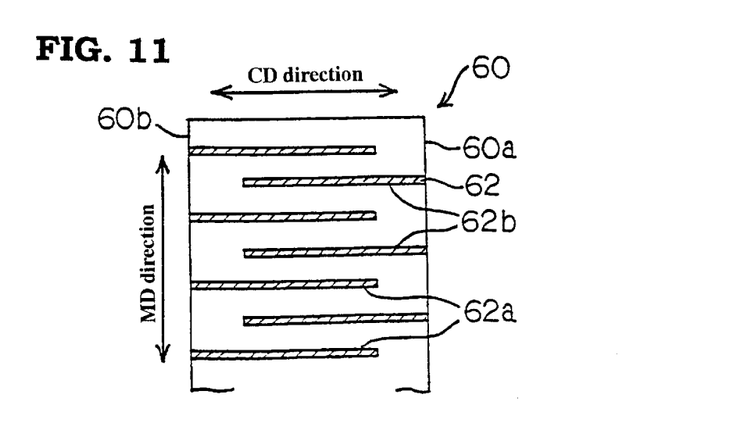
FIG. 11 is a perspective view showing still another embodiment of a nonwoven fabric composing the fastener of the present invention.

In the nonwoven fabric C (60) shown in FIG. 11, the emboss pattern is formed over the entire width of the nonwoven fabric C by alternately arranging linear emboss lines 62a in parallel to the CD direction and away by a predetermined distance from one side edge 60a of the nonwoven fabric C (60) and linear emboss lines 62b in parallel to the CD direction and away by a predetermined distance from the other side edge 60b of the nonwoven fabric C (60). The predetermined distances for the respective emboss lines 62a, 62b away from the side edges 60a, 60b are preferably 5 mm or less. That is, the emboss pattern, as a whole, according to this embodiment intersect with the MD direction widthwise (CD direction) over the entire area of the nonwoven fabric C.

Figure 12:
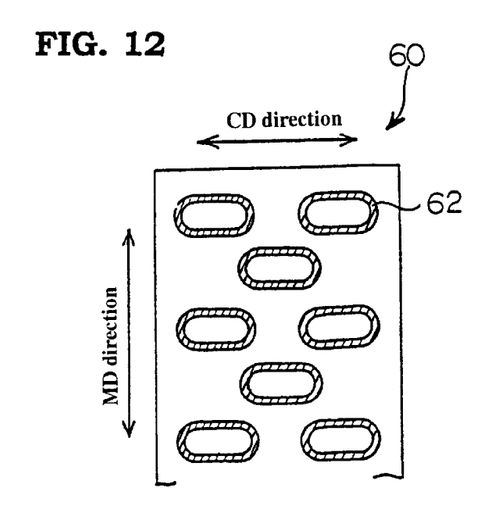
FIG. 12 is a perspective view showing still another embodiment of a nonwoven fabric composing the fastener of the present invention.

In the nonwoven fabric C (60) shown in FIG. 12, the emboss pattern is formed over the entire width of the nonwoven fabric C only excluding opposite sides thereof by arranging a plurality of emboss lines 62 which are each arranged in such a manner as to form a hollow elliptical configuration.

Figure 13:
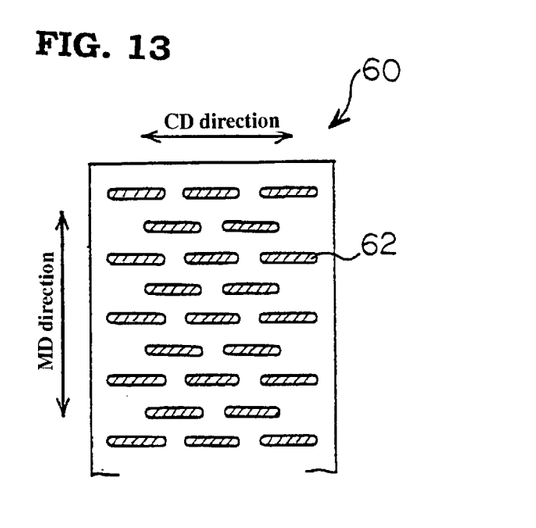
FIG. 13 is a perspective view showing still another embodiment of a nonwoven fabric composing the fastener of the present invention.

In the nonwoven fabric C (60) shown in FIG. 13, the emboss pattern is formed over the entire width of the nonwoven fabric C only excluding opposite sides thereof by arranging a plurality of elliptical emboss lines 62.

Figure 14:
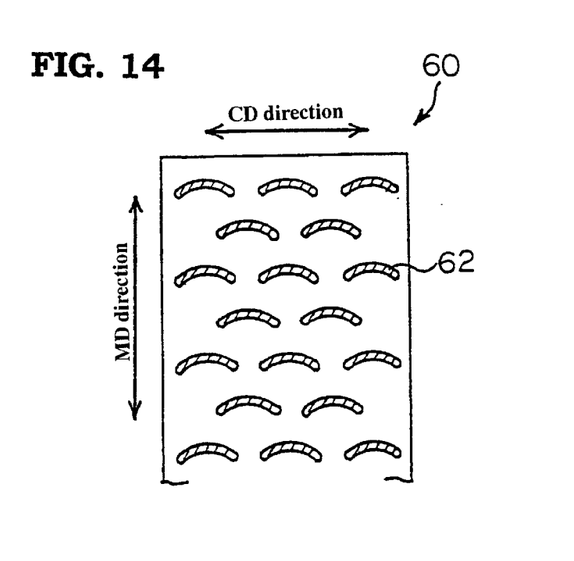
FIG. 14 is a perspective view showing still another embodiment of a nonwoven fabric composing the fastener of the present invention.

In the nonwoven fabric C (60) shown in FIG. 14, the emboss pattern is formed over the entire width of the nonwoven fabric C only excluding opposite sides thereof by arranging a plurality of arcuate emboss lines 62. It should be noted here that, in FIGS. 12 through 14, the opposite sides of the nonwoven fabric C where no emboss pattern is formed, are preferably 5 mm or less from each side end edge of the nonwoven fabric C.

In the nonwoven fabric C according to this embodiment, the width of each emboss line in the emboss pattern is preferably 0.1 to 4 mm and the distance between the adjacent emboss lines is preferably 3 to 40 mm. The area forming the emboss pattern is preferably 5 to 50% in the entire nonwoven fabric C.

Since the nonwoven fabric C according to this embodiment is constructed in the manner as described above, the engaging force with respect to the male material is high, fluffing is generated only very slightly and productivity is enhanced.

The nonwoven fabric C according to this embodiment can be manufactured in the following manner. That is, the nonwoven fabric C can be obtained by first obtaining a raw nonwoven fabric through the airthrough process or the like in which after a fiber web is formed in accordance with a normal method, a hot air of 120 to 150° C. is supplied to the fiber web for 5 to 10 seconds at a velocity of 1 to 2 m/sec and thereafter, subjecting the raw nonwoven fabric to embossing treatment. The embossing treatment is preferably carried out under the following conditions;

processing temperature: 50 to 200° C.
linear pressure: 5 to 120 kPa·m (kN/m)
embossing treatment velocity: 3 to 150 m/min.

It should be noted that the emboss patterns according to this embodiment are not limited to the above pattern and many changes and modifications can be made without departing from the gist (or subject matter) of the present invention. For example, in the embodiments shown in FIGS. 12 and 13, the configuration of the emboss line may be circle.

By providing the nonwoven fabric with the emboss patterns as mentioned above, bulkiness of the airthrough (in other words, easiness of wrapping of the male material of a mechanical fastener) cannot be impaired, and generation of fluffing can be prevented.

As the main fibers composing the nonwoven fabrics A, B and C, short staple fibers, long fiber filaments and the like can be used. Also, sheath-core or side-by-side conjugated fibers and the like can be used. As the material composing the fibers, various types of thermoplastic resins are used.

Particularly, as the main fibers composing the nonwoven fabrics A, B and C, the sheath-core conjugated fibers are preferably used. Among all, those sheath-core conjugated fibers composed of a resin component of the same series are preferably used. The term "resin component of the same series" used herein refers to two kinds of resins or resin mixture in which chemical structures of the resin components composing the sheath component and the core component, respectively, are similar (namely, main chemical structures are the same) to each other and which are compatible to each other. In this case, an interface strength between the core component and the sheath component is preferably larger than the above-mentioned joining point strength. In the case where the nonwoven fabrics A, B and C are composed of two or more kinds of fibers, the main composite fibers are preferably sheath-core conjugated fibers composed of such resin components of the same series and it is particularly preferable that the ratio of the conjugated fibers is 50 wt % or more.

Examples of a specific combination of the core component and the sheath component may include a combination in which polypropylene (PP) is used as the core component and a low melting point PP is used as the sheath component, a combination in which polyethylene terephthalate (PET) is used as the core component and a low melting point PET is used as the sheath component, and the like. It should be noted, however, the combination is not limited to the above and many other combinations can freely be used without departing from the gist (or subject matter) of the present invention.

The above resin components include resin mixtures (so-called blended matters). Accordingly, a resin mixture in which the PET is used as the core component and the sheath component contains the PET as its main component and a resin mixture in which the PP is used as the core component and the sheath component contains the PP as its main component, are also accepted. Examples of the resin mixture in which the PET is used as a main component include a resin mixture composed by mixing polyethylene (PE) with a 100 wt. part of PET in the mixing ratio of 100 wt. part or less, and the like. Examples of the resin mixture in which the PP is used as a main component include a resin mixture obtained by polymerizing a 2 to 8 wt. part of ethylene monomer with a 100 wt. part of propylene monomer, and the like. The composing ratio (weight ratio) of the core component and the sheath component in the conjugated fiber is generally preferably 20 to 80:80 to 20 and particularly preferably 30 to 70:70 to 30.

A melting point of the sheath component in the above-mentioned conjugated fiber is preferably lower by 10 to 120° C. than a melting point of the core component. For example, it is preferred that the melting point of the core component is 125 to 260° C. and the melting point of the sheath component is 90 to 150° C.

Specific examples of the conjugated fiber include a sheath-core conjugated fiber in which the core component is the PP having a melting point of 150 to 170° C. and the sheath component is a low melting point PP having a melting point of 130 to 150° C. (however, the melting point of the PP is lower than the melting point of the core component); a sheath-core conjugated fiber in which the core component is the PE having a melting point of 120 to 140° C. and the sheath component is the PE having a melting point of 90 to 120° C.; a sheath-core conjugated fiber in which the core component is the PET having a melting point of 250 to 270° C. and the sheath component is a low melting point PET having a melting point of 70 to 180° C. , and the like.

Examples of other fibers which can be used together with the main fiber in the above-mentioned nonwoven fabrics A, B and C include a normal polyester fiber, a normal polypropylene fiber, a normal rayon fiber, a normal acrylic fiber, a normal cotton fiber, a normal nylon fiber, a normal conjugated fiber of a PP/PE (core/sheath) structure, a normal conjugated fiber of a PET/PE (core/sheath) structure, a normal polyvinyl alcohol (PVA) fiber and the like.

It is preferred that the main fiber of the adhesive layer 53 in the nonwoven fabric B is a conjugated fiber having a sheath-core structure and both the core component and the sheath component are fibers of the same series. In order not to cause an interface peel-off between the engagement layer and the adhesive layer when the male material is detached, it is preferred to use the core/sheath same series fibers composing the respective layers (example: in the case where the main fiber of the engagement layer is PP/PP, that of the adhesive layer is preferably PP/PP rather than PET/PET).

The above-mentioned other fibers which can be used together with the main fibers in the adhesive layer 53 in the above-mentioned nonwoven fabric B, the same fibers as the above-mentioned other fibers used in the engagement layer 52, can be used.

Figure 15:
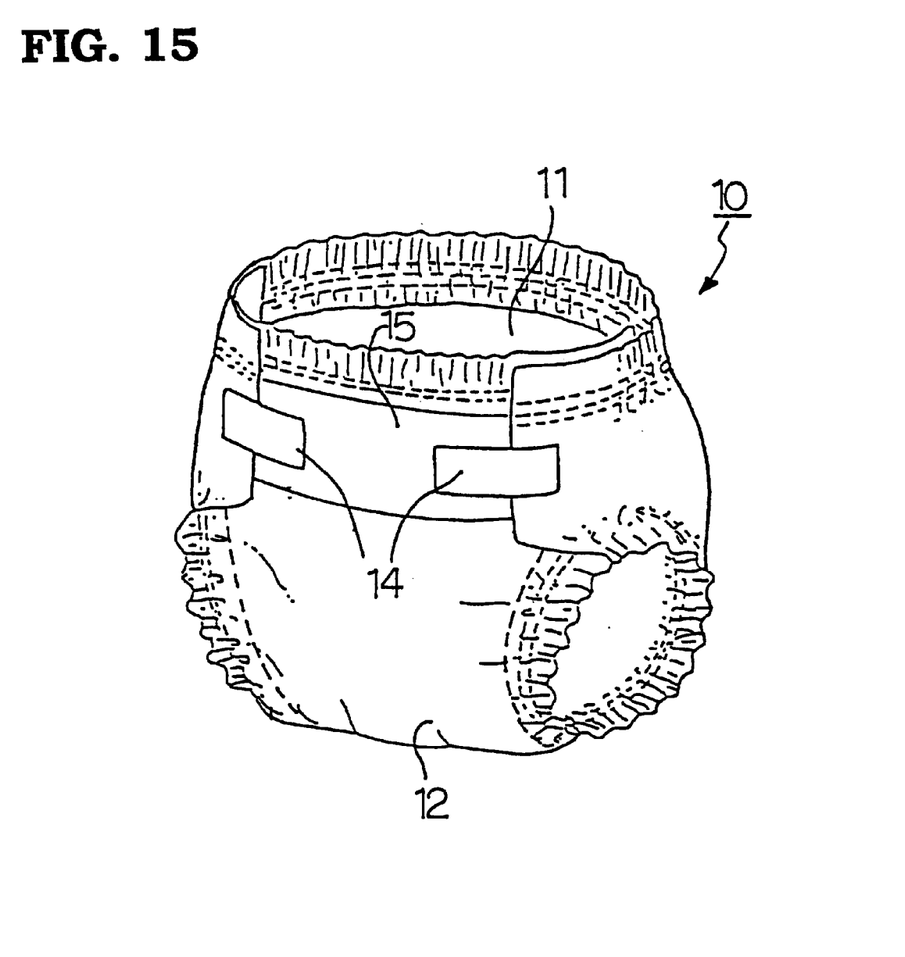
FIG. 15 is a perspective view showing a disposable diaper (absorbent article) to which the fastener of the present invention is applied.

A specific example of application of the fastener according to the present invention will now be described by taking a disposable diaper as one example of an absorbent article and with reference to FIG. 15. FIG. 15 is a perspective view showing a disposable diaper to which the fastener of the present invention is applied.

A disposable diaper 10 shown in FIG. 15 comprises a liquid-permeable topsheet 11, a liquid-impermeable backsheet 12 and a liquid-retentive absorbent core (not shown)

interposed between the topsheet 11 and the backsheet 12, fastening tape 14 for the use of securement being arranged at each of opposing left and right side edge regions of a back-side zone. A landing tape 15 capable of being secured to the fastening tape 14 is disposed on the backsheet 12 in a stomach-side zone. By securing the fastening tape 14 and the landing tape 15 together, they are use as a securing means in the disposable diaper 10. When the disposable diaper is to be put on the user, the fastening tape 14 is secured to the top of the landing tape 15 as shown in FIG. 15. As the fastening tape 14, the above-mentioned male material in the fastener of the present invention is used, and as the landing tape 15, the female material composed of the nonwoven fabric A, B or C is used. The fastening tape 14 and the landing tape 15 as the securing means are required to have a securing force just large enough to prevent the fastening tape 14 from peeling off the landing tape 15 while the disposable diaper 10 is worn by the user. It is also required for the fastening tape 14 and the landing tape 15 not to decrease the securing force even after repeated attachment and detachment. Since the fastener of the present invention can fully satisfy all these requirements, they are very suited to be used as a securing means in the disposable diaper 10. It should be noted that in the disposable diaper shown in FIG. 15, the female material in the fastener of the present invention may be used as the fastening tape 14 and the male material may be used as the landing tape 15.

In the disposable diaper according to this embodiment, since the landing tape 15 or the fastening tape 14 is composed of the nonwoven fabric A, B, C, feeling is not degraded and nice fit is ensured. Moreover, according to the female material composed of the nonwoven fabric B, since there is no fear that adhesive agent tends to exude, the surface of the landing tape 15 or the fastening tape 14 does not get sticky.

Although the fastener of the present invention and the absorbent article using the fastener have hereinbefore been described in the form of preferred embodiments, the present invention should not be limited to those embodiments and many changes and modifications can be made without departing from the gist (or subject matter) of the present invention. For example, the configuration of the hook of the male material in the fastener of the present invention is not limited to those mentioned above, and a variety of configurations may be used selectively.

Aside from its application to the disposable diaper, the fastener of the present invention can likewise be applied to those which require a fastening of two members such as, for example, clothing, shoes, toys, stationery, and the like.

In the absorbent article of the present invention, instead of using, for example, the female material composed of the nonwoven fabric of the present invention as the landing tape, it may be used as the backsheet of a disposable diaper or otherwise it may be adhered to the entire surface of the backsheet. In the case where the female material of the present invention is used in the manner just mentioned, a cloth-like hand feel can be obtained and the diaper can easily be rolled up when it is to be discarded.

EXAMPLES

The fastener of the present invention will now be described in the form of examples in more detail and its effectiveness will also be exemplified. It should be noted, however, that the scope of the present invention is, by no means, limited to those examples.

Examples 1 and 2 and Comparative Examples 1 and 2

By using those shown in Table 1 as the male material and airthrough nonwoven fabrics composed of the sheath-core conjugated fibers shown in Table 1 as the female material, fasteners were manufactured, respectively. Engaging force in an early stage and after repeated attachment and detachment was measured with respect to the fasteners thus obtained and the degree of fluffing was evaluated. The results are shown in Table 1.

<Measuring Method of Engaging Force>

A nonwoven fabric is cut into a size of 5 cm×5 cm and the same was adhered to the top of an outer layer nonwoven fabric (backsheet) of Merries Pants (merchandise name of a disposable diaper manufactured by Kao Corp.) using a double coated adhesive tape. Similarly, a male material was cut into a size of 3 cm×3 cm and its reverse surface side was adhered to a mount having a size of 3 cm×3 cm. Moreover, a base material film having a same size as the male material was adhered to the top of the mount. By doing so, a male material sample was made, in which a portion composed of only the mount has a width of 10 mm on one end side.

Then, this male material sample was placed on the nonwoven fabric in a standstill manner only excluding the 10 mm area (the portion composed of only the mount) of its one end and a roller of 1 kg was moved reciprocally on the male material sample once to cause the male material sample to be pressingly adhered to the nonwoven fabric. Thereafter, the male material sample was pulled at the rate of 300 mm/min in the same direction as the longitudinal direction of the male material sample by holding the above-mentioned one end and the force required for the sample to be peeled off the nonwoven fabric was measured. The same procedure was carried out ten times and an average value thereof was served as an early stage engaging force. The engaging force after repeated attachment and detachment was obtained by repeating the same procedure ten times with respect to the female sample and serving the measured value obtained only at the last 10th procedure as the objective engaging force. For data processing of the measured data, the peel-off test mode data processing software of Orientic Corp [merchandise name: "MP-100P" (MS-DOS) version 43.1] was used and the engaging force was evaluated with the "5 points average load value" contained in it.

It should be noted that the mount and the base material film can be optionally selected inasmuch as the male material can be secured thereto.

<Evaluating Method of Fluffing>

The engaging force after repeated attachment and detachment was measured, and then, fluffing of the nonwoven fabric was evaluated in five grades by visually observing the surface of the nonwoven fabric.

1: no fluffing
2: slight fluffing
3: medium fluffing
4: heavy fluffing
5: breakage of nonwoven fabric

| | Male Material | | | | Female Material | | | Engaging force (gf) | | |
|---|---|---|---|---|---|---|---|---|---|---|---|
| | | | | Hook | | | Joining | | | After | |
| | Configuration | Density (pc/cm) | Height (μm) | width D (μm) | Fiber | Fineness (d) | point strength (cN) | basis wt. (g/m²) | Early stage | repeated attachment/ detachment | Fluffing |
| Ex. 1 | FIG. 2 | 298 | 400 | 140 | PP/PP sheath-core airthrough method | 8 | 3.2 | 41 | 75 | 72 | 1 |
| Ex. 2 | FIG. 3 | 190 | 440 | 195 | PET/PET sheath-core airthrough method | 10 | 3.4 | 40 | 78 | 73 | 1 |
| Comp. Ex. 1 | FIG. 2 | 298 | 400 | 140 | PP/PP sheath-core airthrough method | 2 | 1.3 | 42 | 86 | 43 | 4 |
| Comp. Ex. 2 | FIG. 2 | 420 | 212 | 77 | PP/PP sheath-core airthrough method | 8 | 3.2 | 41 | 23 | 18 | 1 |

As apparent from Table 1, any of the fasteners (invented product), in which the female material is composed of the nonwoven fabric A according to the Examples 1 and 2, has a high engaging force both in the early stage and after repeated attachment and detachment and has only slight fluffing. In contrast, the fastener according to the Comparative Example 1 has a high engaging force in the early stage but its engaging force is lowered to about a half after repeated attachment and detachment and has very heavy fluffing. Although the fastener according to the Comparative Example 2 has only slight fluffing, it has a very small engaging force in the early stage and its engaging force is lowered after repeated attachment and detachment.

Examples 3 and 4, and Comparative Example 3

The engagement layer and the adhesive layer were composed of an airthrough nonwoven fabric which is made of the fiber shown in Table 2 and which have the basis weights shown in Table 2. Nonwoven fabrics were manufactured in accordance with the above-mentioned manufacturing method, using the airthrough nonwoven fabric forming the obtained engagement layer and the airthrough nonwoven fabric forming the obtained adhesive layer.

The air permeability and the fusing point strength were measured with respect to the obtained nonwoven fabrics in accordance with the above-mentioned measuring method. The engaging force and the fluffing were evaluated in the following manner. Moreover, the exuding strength of the adhesive agent was measured. The results are shown in Table 3.
<Evaluating Method of Engaging Force> and <Evaluating Method of Fluffing> were the same methods as used in the above-mentioned [Examples 1 and 2 and Comparative Examples 1 and 2]. An average value after ten times repeated measurements was served as the engaging force.
<Measurement of Exuding Strength of Adhesive Agent>

Adhesive agent [SBS (styrene-butadiene-styrene block copolymer) series] was coated on the adhesive layer of the obtained nonwoven fabric at 25 g/m² and a heat roll nonwoven fabric (22 g/m² composed of a PP fiber (1.8 d) was affixed to the coating surface under the load of 0.5 g/cm².

Then, another heat roll nonwoven fabric was overlapped on the engagement layer of the nonwoven fabric and stored for one day under the atmosphere of 50° C. and under pressure of 200 g /cm². A 180° C. peel test between the engagement layer and the heat roll nonwoven fabric was carried out (pull rate 300 m/min) using a Tensilon tensile test machine and the exuding strength was measured.

Those having an exuding strength (cN/50 mm) of less than 5 cN/50 mm were indicated by ○ and those having an exuding strength of 5 cN/50 mm or more were indicated by X.

TABLE 2

| | | Used fiber (fineness) | | Basis weight |
|---|---|---|---|---|
| Ex. 3 | Engagement layer | PP/PP | (8 d) | 25 g/m² |
| | Adhesive layer | PP/PP | (3 d) | 15 g/m² |
| Ex. 4 | Engagement layer | PET/PET | (10 d) | 25 g/m² |
| | Adhesive layer | PET/PET | (4 d) | 15 g/m² |
| Comp. Ex. 3 | Engagement layer | PP/PP | (8 d) | 20 g/m² |
| | Adhesive layer | PP/PP | (8 d) | 20 g/m² |

Note:
PP represents polypropylene
PET represents polyethylene terephthalate

TABLE 3

| | Permeability (cc · cm⁻² · sec⁻¹) | Fusing point (gf) | Engaging strength (gf) | Fluffing | Exuding strength of adhesive agent (cN · 50 mm⁻¹) |
|---|---|---|---|---|---|
| Ex. 3 | 330 (○) | 5.2 (◎) | 120 (○) | 1 | 2 (○) |
| Ex. 4 | 290 (○) | 3.9 (○) | 150 (◎) | 2 | 1 or less (○) |
| Comp. Ex. 3 | 400 or more (X) | 5.0 (◎) | 117 (○) | 1 | 25 (X) |

Examples 5 and 6 and Comparative Examples 4 and 5

An airthrough nonwoven fabric having a basis weight shown in Table 4 was manufactured using the fibers shown in Table 4 and in accordance with the manufacturing method shown in Table 4 and a raw nonwoven fabric was obtained. The obtained raw nonwoven fabric was subjected to embossing treatment (emboss patterns of Examples 5 and 6 and Comparative Example 5 are the emboss pattern shown in FIG. 1) under the conditions of a processing temperature of 150° C. and a linear pressure of 70 kPa·m and a desired nonwoven fabric was obtained. The nonwoven fabric of Comparative Example 4 was a nonwoven fabric made by a heat roll method and no embossing treatment was applied thereto. A dot-like emboss pattern is formed on the nonwoven fabric of Comparative Example 4. The engaging force and fluffing were evaluated with respect to the obtained nonwoven fabrics in the following manner. The results are shown in Table 5.

<Evaluating Method of Engaging Force> and <Evaluating Method of Fluffing> were the same methods as used in the above-mentioned [Examples 1 and 2 and Comparative Examples 1 and 2].

TABLE 4

|  | Used fiber [mixing ratio] (fineness × fiber length) | Thickness (mm) | Manufacturing method | Elongation (%) | Embossing* | Basis weight (g/m$^2$) |
|---|---|---|---|---|---|---|
| Ex. 5 | PP/PE [50/50] (4 d × 51 mm) | 2.0 | airthrough | 45 | Yes | 40 |
| Ex. 6 | PP/PP [40/60] (4 d × 51 mm) PET/PE [50/50] (4 d × 51 mm) mixing ratio between PP/PP and PET/PE = 1:1 | 2.2 | airthrough | 53 | Yes | 40 |
| Comp. Ex. 4 | PP/PE [50/50] (4 d × 51 mm) | 0.3 | heat roll | 68 | No | 40 |
| Comp. Ex. 5 | PP/PE [50/50] (4 d × 51 mm) | 2.0 | airthrough | 92 | Yes | 40 |

Note:
PP represents polypropylene
PE represents polyethylene
PET represents polyethylene terephthalate
*Embossing treatment is applied after a raw nonwoven fabric is obtained

TABLE 5

|  | Engaging force (gf) | | Fluffing | |
|---|---|---|---|---|
|  | Early stage | After repeated | Early Stage | After repeated |
| Ex. 5 | 100 (○) | 95 (○) | slight (○) | slight/medium (○) |
| Ex. 6 | 115 (◎) | 103 (◎) | slight/medium (○) | medium (○) |
| Comp. Ex. 4 | 47 (X) | 55 (X) | very slight (◎) | very slight (◎) |
| Comp. Ex. 5 | 111 (◎) | 90 (○) | heavy (X) | very heavy (X) |

It should be noted that the present invention includes the fasteners and the absorbent articles according to the following embodiments ①to ⑫.

① A fastener comprising a male material, having many hooks, of a mechanical fastener and a female material, made of nonwoven fabric, of the mechanical fastener, the male material engaging the female material, wherein many hooks in the male material have a density of 100 to 1000 pieces/cm$^2$, a height of 300 to 1500 μm and a width of 100 to 500 μm. (the invention according to claim 1)

② The fastener of the above ①, wherein the nonwoven fabric composing the female material has a basis weight of 20 to 80 g/m$^2$ and a fineness, of 4 to 15 deniers, of a composite fiber thereof. (the invention according to claim 2)

③ The fastener of the above ① or ②, wherein the nonwoven fabric is an airthrough nonwoven fabric.

④ The fastener of the above ① or ②, wherein the nonwoven fabric composing the female material is composed by laminating an engagement layer engaged with the male material and an adhesive layer adhered to a base material, the engagement layer and the adhesive layer are composed of an airthrough nonwoven fabric, and a fineness of a main fiber composing the engagement layer is larger than a fineness of a main fiber composing the adhesive layer.

⑤ The fastener of one of the above ① to ④, wherein the main composite fibers composing the nonwoven fabric is 3 cN or more in joining point strength.

⑥ The fastener of one of the above ① to ⑤, wherein the nonwoven fabric composing the female material is composed by subjecting a raw nonwoven fabric to embossing treatment and elongation thereof, at the time when a load of 2 N/25 mm is incurred in a CD direction, is 75% or less of the raw nonwoven fabric.

⑦ The fastener of the above ⑥, wherein an emboss pattern formed by the embossing treatment is formed in such a manner as to intersect a MD direction at least over an entire width thereof only excluding opposite sides thereof.

⑧ The fastener of the above ⑥ or ⑦, wherein the raw nonwoven fabric is an airthrough nonwoven fabric having a thickness of more than 0.4 mm.

⑨ An absorbent article comprising a liquid-permeable topsheet, a liquid-impermeable backsheet and a liquid-retentive absorbent core interposed between the topsheet and the backsheet, a fastening tape for the use of securement being arranged at each of opposing left and right side edge regions of a back-side zone, a landing tape capable of being secured to the fastening tape being arranged at a stomach-side zone, wherein a male material, having many hooks, of a mechanical fastener is used as the fastening tape, the many hooks having a density of 100 to 1000 pieces/cm$^2$, a height of 300 to 1500 μm and a width of 100 to 500 μm, and a female material, made of nonwoven fabric, of the mechanical fastener is used as the landing tape, or otherwise, the female material is used as the fastening tape and the male material is used as the landing tape. (the invention according to claim 7)

(10) The absorbent article of the above (9), wherein the nonwoven fabric composing the female material has a basis weight of 20 to 80 g/m², a fineness, of 4 to 15 deniers, of the fibers composing the nonwoven fabric. (the invention according to claim 8)

(11) The absorbent article of the above (9) or (10), wherein the nonwoven fabric composing the female material is composed by laminating an engagement layer engaged with the male material and an adhesive layer adhered to a base material, the engagement layer and the adhesive layer are composed of an airthrough nonwoven fabric, and a fineness of a main fiber composing the engagement layer is larger than a fineness of a main fiber composing the adhesive layer.

(12) The absorbent article of one of the above (9) to (11), wherein the nonwoven fabric composing the female material is composed by subjecting a raw nonwoven fabric to embossing treatment and elongation thereof, at the time when a load of 2 N/25 mm is incurred in a CD direction, is 75% or less of the raw nonwoven fabric.

Industrial Applicability

As described hereinbefore, according to the present invention, there can be obtained a fastener which has a high engaging force and which generates fluffing only very slightly.

Moreover, according to the present invention, there can be obtained a fastener in which lowering of the engaging force after repeated attachment and detachment can be prevented effectively.

Furthermore, according to the present invention, there can be obtained a fastener in which productivity is high and which can be manufactured at a low cost.

In addition, according to the present invention, there can be obtained an absorbent article which can provide nice fit without sacrificing the feeling thereof.

What is claimed is:

1. A fastener comprising a male material, having many hooks, of a mechanical fastener and a female material, made of nonwoven fabric, of the mechanical fastener, said male material engaging said female material, wherein many hooks in said male material have a density of 100 to 1000 pieces/cm², a height of 300 to 1500 μm and a width of 100 to 500 μm; and wherein said nonwoven fabric composing said female material is composed of a laminate of an engagement layer engaged with said male material and an adhesive layer adhered to a base material, said engagement layer and said adhesive layer are each composed of an airthrough nonwoven fabric having fibers, and a fineness of a main fiber composing said engagement layer is larger than a fineness of a main fiber composing said adhesive layer.

2. A fastener according to claim 1, wherein said nonwoven fabric composing said female material has a basis weight of 20 to 80 g/m² and a fineness, of 4 to 15 deniers, of a composite fiber thereof.

3. A fastener comprising a male material, having many hooks, of a mechanical fastener and a female material, made of nonwoven fabric, of the mechanical fastener, said male material engaging said female material, wherein many hooks in said male material have a density of 100 to 1000 pieces/cm², a height of 300 to 1500 μm and a width of 100 to 500 μm; and wherein said nonwoven fabric composing said female material is composed of a raw nonwoven fabric subject to embossing treatment and elongation thereof, at the time when a load of 2 N/25 mm is incurred in a CD direction, is 75% or less of said raw nonwoven fabric.

4. A fastener according to claim 3, wherein an emboss pattern formed by said embossing treatment intersects a MD direction at least over an entire width thereof only excluding opposite sides thereof.

5. A fastener according to claim 3, wherein said nonwoven fabric composing said female material has a basis weight of 20 to 80 g/m² and a fineness, of 4 to 15 deniers, of a composite fiber thereof.

6. An absorbent article comprising a liquid-permeable topsheet, a liquid-impermeable backsheet and a liquid-retentive absorbent core interposed between said topsheet and said backsheet, a fastening tape for the use of securement being arranged at each of opposing left and right side edge regions of a back-side zone, a landing tape capable of being secured to said fastening tape being arranged at a stomach-side zone, wherein a male material, having many hooks, of a mechanical fastener is used as said fastening tape, said many hooks having a density of 100 to 1000 pieces/cm², a height of 300 to 1500 μm and a width of 100 to 500 μm, and a female material, made of nonwoven fabric, of said mechanical fastener is used as said landing tape, or otherwise, said female material is used as said fastening tape and said male material is used as said landing tape; and wherein said nonwoven fabric composing said female material is composed of a laminate of an engagement layer engaged with said male material and an adhesive layer adhered to a base material, said engagement layer and said adhesive layer are each composed of an airthrough nonwoven fabric having fibers, and a fineness of a main fiber composing said engagement layer is larger than a fineness of a main fiber composing said adhesive layer.

7. An absorbent article according to claim 6, wherein said nonwoven fabric composing said female material has a basis weight of 20 to 80 g/m², a fineness, of 4 to 15 deniers, of the fibers composing said nonwoven fabric.

8. An absorbent article comprising a liquid-permeable topsheet, a liquid-impermeable backsheet and a liquid-retentive absorbent core interposed between said topsheet and said backsheet, a fastening tape for the use of securement being arranged at each of opposing left and right side edge regions of a back-side zone, a landing tape capable of being secured to said fastening tape being arranged at a stomach-side zone, wherein a male material, having many hooks, of a mechanical fastener is used as said fastening tape, said many hooks having a density of 100 to 1000 pieces/cm², a height of 300 to 1500 μm and a width of 100 to 500 μm, and a female material, made of nonwoven fabric, of said mechanical fastener is used as said landing tape, or otherwise, said female material is used as said fastening tape and said male material is used as said landing tape; and wherein said nonwoven fabric composing said female material is composed of a raw nonwoven fabric subject to embossing treatment and elongation thereof, at the time when a load of 2 N/25 mm is incurred in a CD direction, is 75% or less of said raw nonwoven fabric.

9. An absorbent article according to claim 8, wherein said nonwoven fabric composing said female material has a basis weight of 20 to 80 g/m², a fineness, of 4 to 15 deniers, of the fibers composing said nonwoven fabric.

* * * * *